United States Patent
Hozumi et al.

(10) Patent No.: US 6,271,426 B1
(45) Date of Patent: *Aug. 7, 2001

(54) PROCESS FOR THE PRODUCTION OF 2,6-DICHLORO-3,5-DI(SECONDARY OR TERTIARY ALKYL)TOLUENE

(75) Inventors: Toshio Hozumi; Takayuki Tanonaka; Hitoshi Takahashi; Hidenori Moe; Masaaki Hiruta; Tadahito Kasami, all of Fukushima (JP)

(73) Assignee: Kureha Kagaku Kogyo K.K., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/981,537
(22) PCT Filed: Jun. 12, 1996
(86) PCT No.: PCT/JP96/01584
§ 371 Date: Apr. 15, 1998
§ 102(e) Date: Apr. 15, 1998
(87) PCT Pub. No.: WO96/41788
PCT Pub. Date: Dec. 27, 1996

(30) Foreign Application Priority Data

Jun. 13, 1995 (JP) .................................. 7-170297

(51) Int. Cl.⁷ .................................................. C07C 22/00
(52) U.S. Cl. ............................................................ 570/209
(58) Field of Search ................................................ 570/209

(56) References Cited

U.S. PATENT DOCUMENTS 4,010,214 * 3/1977 Gelfand ................................ 570/209

FOREIGN PATENT DOCUMENTS

| 0257866 | * 3/1988 | (EP) | 570/209 |
|---|---|---|---|
| 0 424 847 B1 | 1/1996 | (EP) . | |
| 1110029 | * 4/1968 | (GB) | 570/209 |
| 62-153234 | 7/1987 | (JP) . | |
| 2-53743 | 2/1990 | (JP) . | |
| 4-1143 | 1/1992 | (JP) . | |
| 4202148 | 7/1992 | (JP) . | |

* cited by examiner

Primary Examiner—Alan Siegel
(74) Attorney, Agent, or Firm—McDermott, Will & Emery

(57) ABSTRACT

This invention relates to an improved process for producing 2,6-dichloro-3,5-di(secondary or tertiary alkyl)toluene represented by the following formula (I). The process comprises chlorinating 3,5-di(secondary and tertiary alkyl) toluene represented by the following formula (II) by reacting with a chlorinating agent in the presence of a Lewis acid together with an aromatic sulfur compound represented by the formula (III) as a promoter:

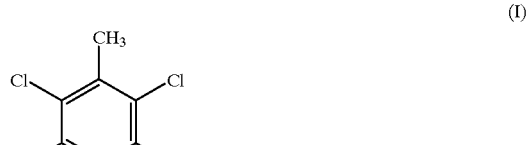

(I)

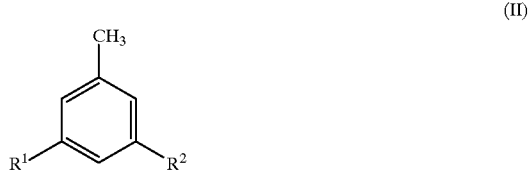

(II)

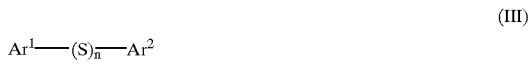

(III)

wherein $R^1$ and $R^2$ are independently a secondary alkyl or tertiary alkyl group, $Ar^1$ and $Ar^2$ are independently an unsubstituted or substituted aromatic ring, and n is 1 or 2.

3 Claims, No Drawings

PROCESS FOR THE PRODUCTION OF 2,6-DICHLORO-3,5-DI(SECONDARY OR TERTIARY ALKYL)TOLUENE

This application is a 371 of PCT/JP96/01584 filed Jun. 12, 1996.

TECHNICAL FIELD

The present invention relates to a process for producing 2,6-dichloro-3,5-di(secondary or tertiary alkyl)toluene which is a useful compound as an intermediate for production of medicines and agricultural chemicals.

BACKGROUND ART 2,6-Dichloro-3,5-di(secondary or tertiary alkyl)toluene which can be produced according to the present invention is known as a useful compound capable of deriving into 2,6-dichlorotoluene which is an intermediate for production of insecticidal 2,6-dichlorobenzamide derivatives or herbicidal 2,6-dichlorobenzonitrile.

Japanese Patent Application Laid-Open No. 53743/1990 discloses that 2,6-dichloro-3,5-di(1,1-dimethylethyl)toluene is obtained in high yield by chlorinating 3,5-di(1,1-dimethylethyl)toluene in the presence of aluminium chloride or ferric chloride together with sulfur, as compared with the case of chlorinating in the presence of sulfur monochloride, zinc sulfide, ferric sulfide or cupric sulfide.

Further, Japanese Patent Application Laid-Open No. 202148/1992 discloses that the yield is improved by choosing the ratio of sulfur and Lewis acid to be used.

However, since there is a demand for higher yield and the process described in the Japanese Patent Application Laid-Open No. 202148/1992 has a problem on operation because of the sulfur being poor soluble in the reaction mixture, more improvement is desired.

On the other hand, William David Watson has proposed chlorination of phenols by reacting with a chlorinating agent in the presence of a Lewis acid together with a sulfur compound (including phenyl sulfide or phenyl disulfide), by which chlorination of high para-selectivity can be conducted (Japanese Patent Application Laid-Open No. 122031/1976).

William David Watson has promptly reported the effect of phenyl sulfide described in the above proposal in Tetrahedron Lett., 1976, 2591–2594., and reported the detail including consideration in J. Org. Chem., 50, 2145–2148 (1985).

The Watson's report discloses chlorination of mono-substituted benzenes other than phenols, but the description of it is only "when chlorobenzene, toluene or ethylbenzene and isopropylbenzene are chlorinated in the presence of aluminium chloride and phenyl sulfide, both of sulfuryl chloride and chlorine produce the same ortho/para ratio" (J. Org. Chem., 50, 2147, right column, paragraph 3). Consequently, it is not found a concrete report concerning effect of coexistence of the Lewis acid and phenyl sulfide or phenyl disulfide upon chlorination of 3,5-di(secondary or tertiary alkyl)toluene.

DISCLOSURE OF THE INVENTION

The present inventors aimed at finding a novel promoter capable of obtaining the target compound in a high yield upon production of 2,6-dichloro-3,5-di(secondary and tertiary alkyl)toluene.

As the result of many studies concerning compounds having a property of dissolving in the reaction mixture, for the purpose of attaining the above mentioned object, the present inventors have found that the 2,6-dichloro-3,5-di(secondary and tertiary alkyl)toluene is obtained in a high yield by using an aromatic sulfur compound represented by the following formula as a cocatalyst of Lewis acid, leading to the present invention.

$$Ar^1-(S)_n-Ar^2 \quad (III)$$

The present invention has the following constitutional characteristics.

The present invention relates to a process for producing 2,6-dichloro-3,5-di(secondary and tertiary alkyl)toluene represented by the formula (I) which comprises chlorinating 3,5-di(secondary and tertiary alkyl)toluene represented by the formula (II) according the following reaction formula by reacting with a chlorinating agent in the presence of a Lewis acid together with an aromatic sulfur compound represented by the formula (III) as a promoter.

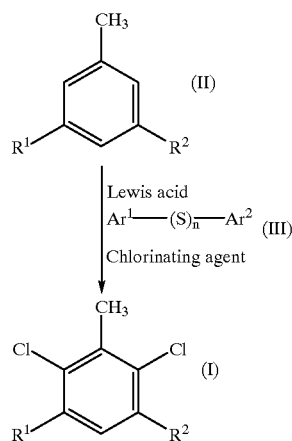

wherein $R^1$ and $R^2$ are independently a secondary alkyl or tertiary alkyl group, $Ar^1$ and $Ar^2$ are independently an unsubstituted or substituted aromatic ring, and n is 1 or 2.

BEST MODE FOR CARRYING OUT THE INVENTION

The present invention will be illustrated in detail in the following.

In the description hereafter, abbreviations shown in [ ] will be used.

2,6-Dichloro-3,5-di(secondary and tertiary alkyl)toluene represented by the formula (I): [referred to as Product (I), hereinafter], 3,5-di(secondary and tertiary alkyl)toluene represented by the formula (II): [referred to as Base material (or substrate) (II), hereinafter], and aromatic sulfur compound represented by (III) [referred to as Promoter (III), hereinafter].

Examples of the base material (II), the chlorinating agent, the Lewis acid and the promoter (III) to be used in the present invention include the following.

As the base material (II), 3,5-di(secondary or tertiary C3–C4 alkyl)toluenes are preferably used. Examples of them include 3,5-di(1-methylethyl)toluene and 3,5-di(1,1-dimethylethyl)toluene.

As the chlorinating agent, chlorine and sulfuryl chloride are used. Chlorine is more preferable to use.

Examples of Lewis acid include aluminium chloride, ferric chloride, antimony trichloride, antimony pentachloride and stannic chloride. Of these, aluminium chloride or ferric chloride is more preferably used.

In the promoter (III), the aromatic ring is preferred to be benzene ring. The benzene ring may be unsubstituted or substituted by 1–5 substituents selected from halogen and C1–C4 alkyl. Examples of them include phenyl sulfide and phenyl disulfide.

In case of using the disulfide, it is possible to produce it by oxidizing the corresponding thiol compound by means of a chlorinating agent in the reaction system.

In the present invention, the solvent is not necessary, but solvents such as carbon tetrachloride, chloroform, nitromethane, nitroethane, nitropropane and nitrobenzene, etc. may be used if the solvent is desired to use.

In the present invention, the chlorination of the base material (II) can be carried out as follows.

A mixture is prepared, which contains a base material (II), 0.0001–2% by weight, and preferably 0.005–0.5% by weight, of a Lewis acid, 0.0006–35% by weight, and preferably 0.06–20% by weight of a promoter (III), based on the base material (II), and if necessary solvents.

The mixture is kept at a reaction temperature of from −10° C. to 70° C., and preferably from 30° C. to 60° C. with sufficiently stirring, and a chlorinating agent is introduced to the mixture to chlorinate so as to be a chlorination degree of 1.4–2.4 and preferably 1.8–2.1.

The chlorination degree means a value obtained by examining composition of the reaction mixture on the basis of the following criteria; that is, chlorination degree of the base material (II) is 0, that of the monochloride is 1, that of the dichloride is 2 and that of the trichloride is 3.

Main side reactions which causes reduction of the yield of the product (I) include dealkylation reaction of the base material (II), isomerization chlorination reaction of the base material (II) and over chlorination reaction (=reaction of forming trichloride).

According to the invention, however, such side reaction can be prevented by chlorinating the base material (II) in the presence of 10–150 times by mol, preferably 20–70 times by mol of the promoter (III) based on 1 mol of Lewis acid, whereby the product (I) of the chlorination degree of about 2 can be obtained in the yield of 90% or more.

There is another characteristic of the present invention. Namely, in the present invention, since the amount of insoluble materials is very small during the reaction and after the reaction, it is easily cooled a part of the reaction solution by the exterior heat exchanger.

Consequently, it is not necessary to control the heat of reaction by adjusting the chlorination rate. Because of using the promoter (III), this process is hardly subjected to restriction by the scale of reaction.

EXAMPLE

In the following, the present invention is illustrated in reference with production examples, but the invention is not limited to these examples unless departing from the spirit of the invention.

In Production Example 1 and 2, the following materials were used as the base material (II), the chlorinating agent, the Lewis acid and the promoter (III).
(1) Base material (II): 3,5-Di(1,1-dimethylethyl)toluene (referred to as "DBT", hereinafter)
(2) Chlorinating agent: Chlorine
(3) Lewis acid: Aluminium chloride
(4) Promoter (III): Phenyl sulfide (used in Production Example 1) and phenyl disulfide (used in Production Example 2)

The end of the reaction was determined on the basis of the chlorination degree obtained by quantitative analysis by means of gas chromatography of a part of the reaction mixture.

Production Example 1

Production of 2,6-dichloro-3,5-di(1,1-dimethylethyl)toluene [Example of Using Phenyl Sulfide as the Promoter]

Into a 4 $m^3$ reactor (the inside being covered with a glass lining) having a jacket equipped with variable turbine blades, a circulation pump for the reaction solution, an exhaust condenser, a vessel for dissolution of the promoter, an exterior heat exchanger and a pot for charging aluminium chloride, 3310 kg (16.23 kmol) of DBT was charged and heated to 40° C., followed by replacing the atmosphere with nitrogen.

0.6 kg (0.0045 kmol) of aluminium chloride was then promptly added to the reactor by means of the pot for charging aluminium chloride. Furthermore, 32 kg (0.172 kmol) of phenyl sulfide was added from the vessel for dissolution of the promoter to the reactor.

With controlling the reaction temperature so as to be 50±10° C., a chlorine gas was introduced into the reactor at the bottom thereof. When the chlorination degree became 2.05, the reaction was stopped. It was necessary to react for 14 hours and 40 minutes till the end of the reaction.

Then, nitrogen was blown into the reaction mixture to remove dissolved gas, followed by washing with water. After the organic phase was dried by sodium sulfate, the composition was analyzed by gas chromatography.

As the result, it was confirmed that 2,6-dichloro-3,5-di(1,1-dimethylethyl)toluene was produced in a yield of 93%.

Production Example 2

Production of 2,6-dichloro-3,5-di(1,1-dimethylethyl)toluene [Example of Using Phenyl Disulfide as the Promoter]

The same procedure was carried out as in Production Example 1 except that 3266 kg (16.01 kmol) of DBT, 1.0 kg (0.0075 kmol) of aluminium chloride and 100 kg (0.459 kmol) of phenyl disulfide were introduced.

The reaction was stopped when the chlorination degree became 2.03. It was necessary to react for 12 hours and 10 minutes till the end of the reaction.

As the result of the same post-treatment and analysis as in Production Example 1, it was confirmed that 2,6-dichloro-3,5-di(1,1-dimethylethyl)toluene was produced in a yield of 90%.

[Industrial Applicability]

2,6-Dichloro-3,5-di(secondary and tertiary alkyl)toluene can be obtained in a high yield without being subject to restriction by the reaction scale, by chlorination of 3,5-di (secondary and tertiary alkyl)toluene in the presence of Lewis acid together with an aromatic sulfur compound represented by the above formula (III) as a promoter.

What is claimed is:

1. A process for producing 2,6-dichloro-3,5-di(tertiary alkyl)toluene represented by the following formula (I) which comprises chlorinating 3,5-di (tertiary alkyl) toluene represented by the following formula (II) by reacting with chlorine in the presence of a Lewis acid together with an aromatic sulfur compound represented by the formula (III) as a promoter, the molar ratio of the promoter to the Lewis acid being in the range of 20–150:

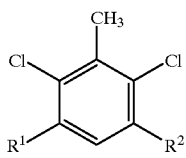
(I)

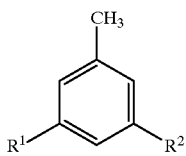
(II)

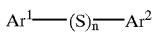
(III)

wherein $R^1$ and $R^2$ are independently a tertiary alkyl group, $Ar^1$ and $Ar^2$ are independently an unsubstituted or substituted aromatic ring, and n is 1 or 2.

2. A process for producing 2,6-dichloro-3,5-di(1,1-dimethylethyl) toluene which comprises chlorinating 3,5-di(1,1-dimethylethyl)toluene by reacting it with chlorine in the presence of an aluminum chloride or ferric chloride Lewis acid together with a phenyl sulfide or phenyl disulfide promoter, the molar ratio of the promoter to Lewis acid being in the range of 20–150.

3. The process according to claim 1, comprising producing the 2,6-dichloro-3,5-di(tertiary alkyl)toluene in a yield of 90% or more.

* * * * *